United States Patent
Mohr et al.

(10) Patent No.: US 9,480,447 B2
(45) Date of Patent: Nov. 1, 2016

(54) INCLINED PHASE GRATING STRUCTURES

(75) Inventors: Juergen Mohr, Sulzfeld (DE); Franz Pfeiffer, Garching (DE); Elena Reznikova, Novosibirsk (RU); Vladimir Nazmov, Linkenheim (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 427 days.

(21) Appl. No.: 13/703,824

(22) PCT Filed: Jun. 15, 2011

(86) PCT No.: PCT/EP2011/059940
§ 371 (c)(1),
(2), (4) Date: Feb. 25, 2013

(87) PCT Pub. No.: WO2011/157749
PCT Pub. Date: Dec. 22, 2011

(65) Prior Publication Data
US 2013/0148780 A1 Jun. 13, 2013

(30) Foreign Application Priority Data
Jun. 17, 2010 (DE) .................. 10 2010 017 425

(51) Int. Cl.
*A61B 6/00* (2006.01)
*G01N 23/00* (2006.01)
*G02B 5/18* (2006.01)
*A61B 6/03* (2006.01)

(52) U.S. Cl.
CPC .............. *A61B 6/484* (2013.01); *A61B 6/4291* (2013.01); *G01N 23/00* (2013.01); *G02B 5/1871* (2013.01); *A61B 6/03* (2013.01); *A61B 6/4092* (2013.01); *A61B 6/502* (2013.01); *A61B 6/504* (2013.01)

(58) Field of Classification Search
CPC ........ A61B 6/03; A61B 6/484; A61B 6/502; A61B 6/504; A61B 6/4092; A61B 6/4291; G01N 23/00; G02B 5/1871
See application file for complete search history.

(56) References Cited

U.S. PATENT DOCUMENTS

| | | |
|---|---|---|
| 6,600,602 B2 | 7/2003 | Kleemann et al. |
| 6,723,474 B2 | 4/2004 | Tomita et al. |
| 7,486,770 B2 | 2/2009 | Baumann et al. |
| 7,564,941 B2 | 7/2009 | Baumann et al. |
| 8,009,796 B2 | 8/2011 | Popescu et al. |
| 2001/0008741 A1 | 7/2001 | Tomita et al. |
| 2002/0024735 A1 | 2/2002 | Kleemann et al. |
| 2004/0223585 A1 * | 11/2004 | Heismann et al. ............. 378/54 |
| 2007/0183579 A1 | 8/2007 | Baumann et al. |

(Continued)

FOREIGN PATENT DOCUMENTS

| | | |
|---|---|---|
| DE | 10025694 A1 | 3/2002 |
| DE | 102008048688 A1 | 3/2010 |
| JP | 2000075117 A | 3/2000 |
| JP | 2001134204 A | 5/2001 |

(Continued)

*Primary Examiner* — Glen Kao
*Assistant Examiner* — Chih-Cheng Kao
(74) *Attorney, Agent, or Firm* — Abel Law Group, LLP

(57) ABSTRACT

Grating interferometer comprising inclined phase grating structures, method for increasing the definition of phase contrast images of interferometers or in applications which are based on the Talbot effect, using inclined phase grating structures, phase gratings wherein the grating structures are positioned at angles on the substrate of the phase grating, method for producing grating structures which are positioned at angles on the substrate of the phase grating, and corresponding uses.

14 Claims, 3 Drawing Sheets

X-ray radiation

Phase grating     Analysis grating

(56) References Cited

U.S. PATENT DOCUMENTS

| | | |
|---|---|---|
| 2007/0183582 A1 | 8/2007 | Baumann et al. |
| 2007/0183583 A1* | 8/2007 | Baumann et al. ............ 378/145 |
| 2009/0092227 A1 | 4/2009 | David et al. |
| 2009/0207416 A1 | 8/2009 | Xiangqian et al. |
| 2010/0080341 A1 | 4/2010 | Popescu et al. |
| 2012/0057677 A1 | 3/2012 | Vogtmeier et al. |
| 2012/0288056 A1 | 11/2012 | Murakoshi et al. |

FOREIGN PATENT DOCUMENTS

| | | |
|---|---|---|
| JP | 2007203064 A | 8/2007 |
| JP | 2007206075 A | 8/2007 |
| JP | 2011206489 | 10/2011 |
| JP | 2011206490 | 10/2011 |
| WO | 2010146498 A1 | 12/2010 |
| WO | WO 2010146498 A1 * | 12/2010 |
| WO | 2011096584 A1 | 8/2011 |

\* cited by examiner

INCLINED PHASE GRATING STRUCTURES

All documents cited in the present application are incorporated into the present disclosure by reference in their entirety.

FIELD OF THE INVENTION

The present invention relates to improvements in the phase gratings in applications that are based on the Talbot effect.

TECHNICAL BACKGROUND

Phase-contrast imaging with X-ray beams is based on a grating-based interferometer, which utilizes the Talbot effect for imaging. To this end, two gratings are positioned parallel to one another, perpendicular to the X-ray beam. The phase grating $g_1$ consists of lines which cause a phase shift of $\pi$ (or $\pi/2$) ($\pi$=3.14159 . . . ) and an X-ray absorption that can be neglected. It acts as a beam splitter and divides the X-ray beams into the +1 and −1 diffractive order. The diffracted beams interfere according to the (fractional) Talbot effect and an interference pattern is created, which is periodic in the directions perpendicular to the grating lines. The interference image has a maximum modulation at the fractional Talbot distances $d_m$:

For parallel beam geometry, $d_m$ is $$d_m = m \frac{p_1^2}{8\lambda},$$

where:
$\lambda$ (lambda)=wavelength,
$p_1$=grating period of $g_1$ (phase grating),
m=odd integer=order of the fractional Talbot distance.

For the conventional cone-beam geometry, $d_m$ changes by the factor $$\frac{l}{l - d_m},$$

where l is the distance of the phase grating from the X-ray source.

In order to determine the position of the interference pattern, it is scanned by the analyzer grating $g_2$, which has strongly absorbing slats with the period $p_2$.

For the cone-beam geometry, $p_2$ emerges from $$p_2 = \frac{l}{l - d_M} \frac{p_1}{A},$$

with A=1 for a phase shift of $\pi/2$ and A=2 for a phase shift of $\pi$ ($\pi$=3.14159 . . . ). As a result, the ratio of the periods $p_1$ and $p_2$ depends on the wavelength, on the selected fractional Talbot distance and on the distance l of the phase grating from the X-ray source.

Since deviations from the ideal period ratio lead to a deterioration of the image quality, a grating set fitted to the period must be selected for each experiment. Since the production of the gratings using micro-technical methods is very complicated, this is very cost intensive. Moreover, the user does not have the option of performing measurements at different Talbot distances using a predetermined grating set and thus matching the measurement set-up to different sensitivities of the objects to be measured. A further problem consists in the fact that, depending on the production method, the period can only be maintained to an accuracy of a few nanometers. By way of example, the positional accuracy of an electron beam writer, which is usually used for creating the primary grating structure, is specified to a few nanometers. In this respect, variations in the period length between phase grating and analyzer grating of a few nanometers are to be expected, particularly in the case of gratings for which an electron beam lithography is necessary in each case.

A person skilled in the art is sufficiently well aware of more detailed information in respect of the described effects and apparatuses; therefore it does not have to be described in any more detail here. US 2007/0183579 A1 and US 2009/0092227 A1 have disclosed to rotate phase gratings about the optical axis in accordance with the direction of incidence of the beams, in order thereby to counteract bothersome moiré patterns.

DE 100 25 694 A1 relates to Littrow configurations when using UV beams (weak UV beams).

US 2009/0207416 A1 describes instruments based exclusively on light (optionally UV and IR), but not on X-ray beams.

In DE 10 2008 048 668 A1, an attempt is made to sidestep the effect of the spreading of the X-ray beam by arranging a plurality of gratings, i.e. what should be achieved by arranging a plurality of gratings next to one another is that the X-ray beams pass straight through the grating structure because these grating structures are perpendicular to the respectively incident X-ray beams.

Object

The object of the present invention is to avoid the disadvantages of the prior art.

In particular, the image quality, for example the phase contrast and focus, should be improved by simple means; interferometers should be usable in a more variable fashion such that there is no need for each experiment to have its own phase grating, resulting in economical advantages.

Solution

This object is achieved by special gratings or grating arrangements for the phase gratings of interferometers, and by corresponding interferometers and methods, and also by uses, in which the grating structure is inclined in relation to the irradiation direction or the optical axis, corresponding to a rotation of the grating about the grating central axis which runs parallel to the grating ribs or a rotation of the individual grating ribs about their respective longitudinal axis which is arranged parallel to the grating central axis.

Terminology

Within the scope of the present invention, the terms "interferometer" and "grating interferometer" relate to instruments which work using the Talbot effect.

DETAILED DESCRIPTION

In the following description and in the following drawings, the same parts or features in the description and in the drawings are denoted by the same numbers. The drawings are not necessarily true to scale. For reasons of clarity and for making the illustration simpler, some features of the invention can be illustrated in a disproportionately large or schematic fashion; it is likewise accordingly possible that some details of conventional or known elements have not been illustrated.

The subject matter of the present invention relates to grating interferometers with inclined phase grating structures.

In particular, the inclined grating structures are obtained by
a) inclining the grating structures in the interferometer set-up with respect to the irradiation direction or optical axis, corresponding to a rotation of the grating about the grating central axis which runs parallel to the grating ribs, and/or
b) producing the grating structures at an incline on the substrate of the phase grating, corresponding to a rotation of the individual grating ribs about their respective longitudinal axis which is arranged parallel to the grating central axis.

Accordingly, the present invention comprises a), b) and a)+b) in three alternative embodiments.

Here, item a) should preferably be understood to mean either
a subsequent desired incline after the installation or
a desired incline during the installation
in order to obtain a specific inclination angle of the phase grating with respect to the irradiation direction or with respect to the optical axis.

A preferred embodiment of the present invention does not mean that there is, and does not comprise, an incline of the grating structures in the interferometer set-up with respect to the irradiation direction or the optical axis as a result of an inadvertent maladjustment. In this embodiment, the present invention relates to deliberately brought about inclinations of the gratings by an inclination with respect to the actual state (e.g. the state as supplied) of the interferometer.

Accordingly, the subject matter of the present invention also relates to the use of inclined grating structures as phase gratings in interferometry.

Furthermore, the subject matter of the present invention relates to a method for increasing the image quality, in particular the focus, of phase-contrast images in interferometers, or in applications that are based on the Talbot effect, characterized in that the following are used as phase gratings:
i) phase gratings which in the interferometer set-up are inclined with respect to the irradiation direction or the optical axis, corresponding to a rotation of the grating about the grating central axis which runs parallel to the grating ribs, and/or
ii) phase gratings, in which the grating structures are arranged at an incline on the substrate of the phase grating, corresponding to a rotation of the individual grating ribs about their respective longitudinal axis which is arranged parallel to the grating central axis.

Accordingly, the present invention comprises i), ii) and i)+ii) in three alternative embodiments.

The subject matter of the present invention likewise relates to phase gratings in which the grating structures are arranged at an incline on the substrate of the phase grating.

Not least, the subject matter of the present invention relates to the uses of the novel phase gratings, interferometers and methods.

In particular, the present invention relates to grating interferometers on synchrotron beam tubes or for X-ray radiation in general.

In the set-up of grating interferometers on synchrotron beam tubes, the differences in the grating periods lie of the order of a few nanometers, typically in the range of 2 nm to 10 nm (i.e. within the tolerance range of the manufacturing process), which corresponds to less than 1% of the period length in the case of periods of a few micrometers. In the case of applications with X-ray tubes, for example in computed tomography, the changes in the period are of the order of a few 10 nm, i.e. in the region of a few percent of the period length.

According to the invention, changes in the period within the aforementioned range can be achieved by placing the phase grating at an incline relative to the beam, corresponding to a rotation of the grating about the grating central axis which runs parallel to the grating ribs. In this case, the change in the period is proportional to the angle of the inclination.

$$p'=(1-\cos \Theta)*p, \Delta p=p*\cos \Theta$$

By way of example, a change in the period of 5 nm in the case of a period length of 2.5 µm requires an inclination of approximately 3.63°.

Changes in the angle when changing the Talbot distance or the wavelength are more likely to be of the order of tenths of a degree and hence in the region below 1 nm.

Such changes in the period, but also already changes in the region of a few nanometers, are already within the tolerance of the production method, as illustrated above. Accordingly, the present invention can thus be used for compensating the manufacturing tolerances during the production, i.e. for error correction.

For changes in the period of e.g. 50 nm (application with X-ray tubes) and periods of 2.5 µm, the inclination angle is approximately 12°.

A first variant i) according to the invention consists of producing the grating structures perpendicularly on a substrate, i.e. the conventional production of conventional phase gratings, and then of inclining the grating structure in the interferometer set-up at the desired angle, corresponding to a rotation of the grating about the grating central axis which runs parallel to the grating ribs.

In this variant, the structures are then inclined with respect to the beam and, in the process, do not generate a rectangular absorption profile.

Depending on the material used and on the energy used within the experiment, the height of the lamella structures of the phase gratings can be significantly more than 50 µm (for example if a plastic or silicon is used). In this case, the lamellae can already be covered in the case of angles of around 1°, and so the intensity profile is no longer unique. If use is made of highly refractive materials as phase gratings (e.g. metals), the height lies in the region of a few micrometers, such that, for example, if the height is 10 µm, changes in the angle with respect to the perpendicular orientation of up to approximately 5° are possible without there being a covering.

Accordingly, it is preferable for metals to be used as phase gratings in this variant i).

Here, use can be made of any metal that can be electroplated, particularly if the gratings are produced by the LIGA method.

It is preferable for use to be made of metals selected from the group consisting of nickel, copper, gold, tungsten or mixtures, alloys and combinations thereof. Copper and nickel are particularly preferred, particularly nickel as metal for the phase gratings.

Accordingly, particular care has to be taken in this variant that the changes in angle have to be matched to the respective conditions; optionally this can be brought about by simple pre-trials.

A second variant ii) according to the invention consists of producing on the substrate the structures with the angle (period length) of a few degrees that is required for the usual or respective set-up, corresponding to a rotation of the individual grating ribs about their respective longitudinal axis which is arranged parallel to the grating central axis, and of installing the substrate into the beam at this angle.

In this case, radiation passes through the structures in a straight line. Since the changes in the angle are very small when the Talbot distance changes and are more likely to lie in the region of less than 1°, these changes can, starting from the already preset angle, be realized with only a small loss of quality in the images. There is no covering even in the case of very high lamella structures and the steepness of the flanks in the absorption profile remains high. In the case of high X-ray energies, this procedure is also advantageous in the case of metal gratings and permits the application of the method to practically all X-ray energies.

This variant ii) renders it possible to avoid the problem of covering, which may occur in the first variant.

Accordingly, this second variant i) is preferred in an embodiment of the present invention.

It is likewise part of the present invention to combine variants i) and ii).

Here, the production of the phase-contrast gratings has no peculiarities and is brought about according to conventional methods such as e.g. the LICA method, by means of UV lithography or by means of an electron beam writer, with UV lithography and electron beam writing being less suitable for relatively high structures (higher than 2-3 µm).

Phase gratings in which the grating structures are not inclined on the substrate can also be produced by dry etching methods (e.g. DRIE) or laser ablation.

Accordingly, the present invention also comprises interferometers in which the phase gratings, either those with a conventional set-up or those with inclined lamella structures, can be regulated or adjusted from the outside, i.e. without it being necessary for the interferometer to be opened.

In this case, the regulation or adjustment can take place in a purely mechanical fashion, for example by means of a control dial, or it can take place automatically in a computer-assisted fashion.

It is possible to regulate the incline of the phase grating very precisely while the measurement is taking place, particularly in the computer-assisted embodiment variant, and so an optimum imaging power can be achieved.

Accordingly, it is self-evident that interferometers according to the invention can also be regulated in different directions from the outside.

A further variant of the present invention comprises interferometers which contain a plurality of phase gratings which can be interchanged and inclined from the outside, i.e. without it being necessary for the interferometer to be opened, for example via control dials or by computer control. The plurality of phase gratings can for example be arranged in the style of a revolver magazine or in the style of a slide-projector carousel.

This is how it is possible to cover a very large angular range and further increase the variability of the interferometers.

A significant advantage of the present invention consists in the fact that the structures for the two gratings can be produced using the same process technology (lithography method) and, as a result of this, starting from the same primary structure (produced by the electron beam writer) and the master mask resulting therefrom. In addition to the fact that the demanded changes in the period can be set very precisely using this and are not subjected to the tolerances of the primary structuring, process-dependent deviations from the intended geometry are transferred in identical fashion onto the two grating structures (phase grating and intensity grating).

In this respect, negative effects as a result of the process-dependent deviations are minimized or even completely compensated for.

The prior art has not disclosed any similar solutions. Until now, every grating structure was produced starting from a primary structure adapted in terms of the period length.

Accordingly, the subject matter of the present invention also relates to a method for producing grating structures inclined on the substrate of the phase grating, corresponding to a rotation of the individual grating ribs about their respective longitudinal axis which is arranged parallel to the grating central axis, in which phase grating G1 and analysis grating G2 for an X-ray interferometer are produced starting from the same master mask, in particular by electron beam lithography (e-beam lithography), characterized in that use is made of a master mask which has the period of the analysis grating G2, the analysis grating G2 is created by direct perpendicular exposure, and the phase grating G1 is created, by oblique exposure or oblique arrangement at an angle, by a projection with the grating period G1.

Here, the decisive feature is that the two gratings are produced from the same master mask and therefore have the same process errors. Inclining the phase grating brings about correspondence of the grating periods; errors in the production of the gratings are averaged out, at least to the greatest extent.

Here, the particular advantages of this method according to the invention can be illustrated as follows:

In the case of a production tolerance of the gratings of e.g. 10 nm (tolerance of the e-beam lithography which is used to produce the grating mask), the periods in the case of independent gratings may deviate by 20 nm in absolute terms or vary by 20 nm over the whole grating structure. In the case of a period of 2 µm, this would mean that a moiré pattern with a period of 100*2 µm=200 µm is created.

If the periods of the two gratings have to differ by 0.1 µm as a result of the fan-shaped X-ray beam, this can be achieved by an inclination at an angle of 3 degrees. Since there is no problem with setting an angle to 0.1 degrees, it is possible to set the period with an accuracy of 4 nm. The period accuracy is 0.3 nm in the case of an accuracy of 0.01 degrees.

However, if the gratings are produced using the same e-beam master mask, it is possible to obtain a significantly higher accuracy than in the case of independently produced gratings, and so significantly fewer moiré patterns are created if use is made of gratings produced by the method according to the invention, and so the imaging power is correspondingly better.

Period variations in the two gratings that were produced by the same e-beam master mask play virtually no role seeing as they are at the same position, and hence longer periods in a bright/dark variation are detected at the point with a larger grating period. This is a problem for gratings that were produced by different masks.

As a result of the present invention it is also possible to use a single phase grating for different measurements.

Accordingly, the present invention constitutes a significant simplification of the method. The present invention can likewise result in considerable savings in terms of costs because fewer phase gratings are required.

In other words, an advantage of the present invention lies in the fact that the phase-contrast gratings enable variable periods as a result of the inclination.

The present invention also relates to phase-contrast tomography with X-ray radiation.

It is particularly advantageous in the present invention that the phase-contrast images become more focused and do not obtain any additional intensity modulations.

The inclined gratings according to the invention can be used in X-ray based systems in medical engineering (e.g. X-ray tomography) and in instruments for non-destructive testing of materials and components.

In one variant of the present invention, the inclined gratings according to the invention can be used in gantry units of computed tomography scanners, in X-ray optical units of micro-CT instruments, in X-ray optical systems for medical radiography (mammography) or angiography.

The various embodiments of the present invention, for example, but not exclusively those of the various dependent claims, can in this case be combined together in any desired fashion.

Description of the Figures:
List of reference signs:
1 Mask (for the production)
2 Photoresist
3 Metal, preferably gold after electroplating
4 Substrate

The figure illustrates a tilt in the case of perpendicularly structured gratings. It shows a phase grating in which the grating structure is produced perpendicularly on a substrate 4 and the grating structure is then inclined at the desired angle in the interferometer set-up.

Figure 1:
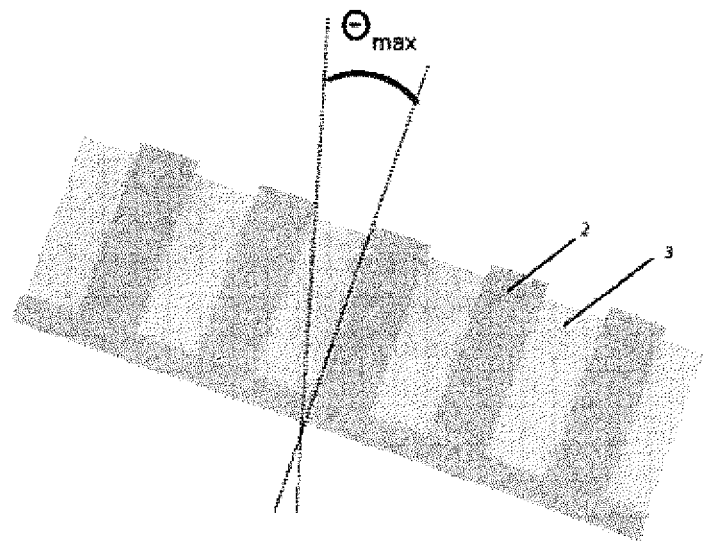
FIG. 1.
Figure 2:
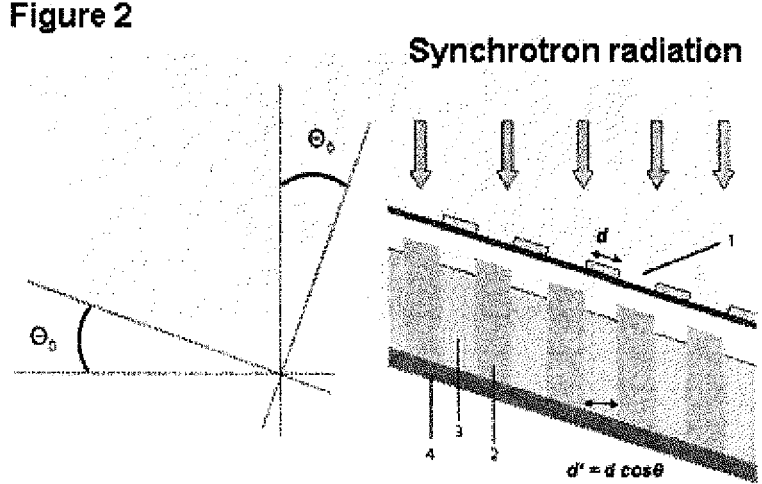
Figure 3:
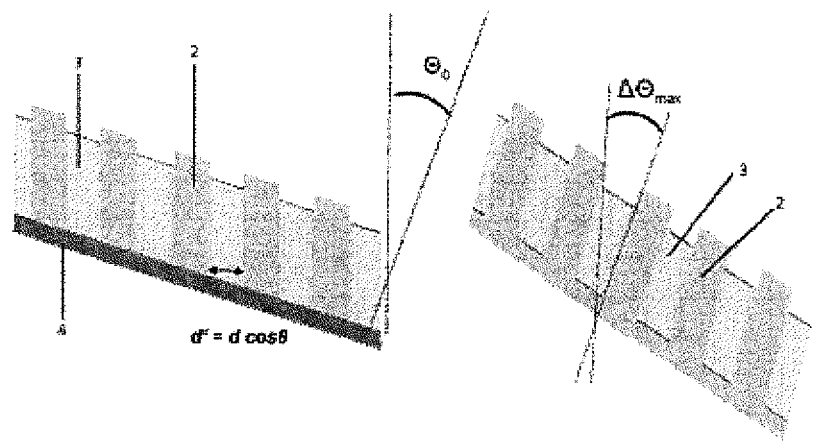
Figure 4:
Figure 5:
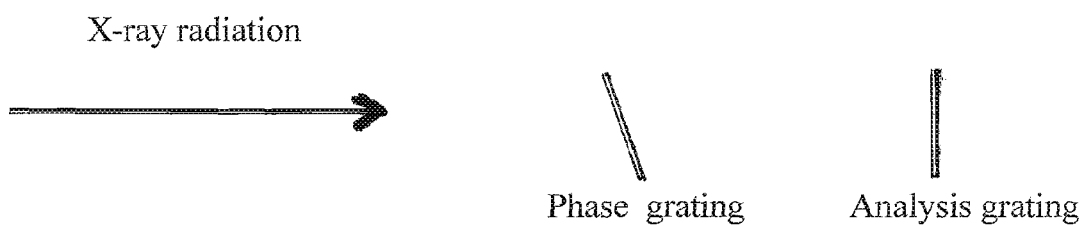

FIG. 2:

FIG. 2 illustrates the second variant according to the invention, in which the structures with the angle (period length) of a few degrees required for the conventional set-up are produced on the substrate 4 and the substrate is installed into the (synchrotron) beam at this angle. Here, the radiation passes through the structures in a straight line.

FIG. 3:

This figure illustrates the advantages of the second variant according to the invention: since the changes in angle are small when the Talbot distance changes and are more likely to lie in the region of less than 1°, these changes can, starting from the already preset angle, be realized with only a small loss of quality in the images. There is no covering even in the case of very high lamella structures and the steepness of the flanks in the absorption profile remains high.

FIG. 4:

Phase-contrast radiography recordings of a coin at 82 keV X-ray energy.

Left: A recording with non-divergence compensated gratings (divergence compensated in this case means inclined and adapted to the situation and period). Right: A recording with almost completely divergence compensated gratings (in this case specifically 5° divergence compensation in the case of a 155 m source distance, a grating period of 2.4 µm and 55 cm distance between the gratings).

It is clearly visible that the phase-contrast images become more focused and do not obtain any additional intensity modulations.

FIG. 5

This figure shows in a purely schematic fashion a phase grating and an analysis grating of an interferometer of the present invention wherein the analysis grating is arranged perpendicular to X-radiation to be analyzed and the phase grating is inclined with respect to the X-ray radiation.

What is claimed is:

1. A grating interferometer, wherein the interferometer makes use of the Talbot effect and comprises a phase grating and an analysis grating for X-ray radiation, and wherein, when the analysis grating is arranged to be perpendicular to X-ray radiation to be analyzed, the phase grating is inclined with respect to the X-ray radiation, the inclination of the phase grating with respect to the X-ray radiation corresponding to a rotation of the phase grating about a grating central axis which runs parallel to grating ribs.

2. The grating interferometer of claim 1, wherein the inclination of the phase grating with respect to the irradiation direction can be regulated or set from the outside.

3. The grating interferometer of claim 1, wherein the interferometer comprises a plurality of interchangeable phase gratings.

4. A method of interferometry, wherein the method comprises carrying out the interferometry by using the interferometer of claim 1.

5. The method of claim 4, wherein image quality is increased or improved as a result of using the inclined phase grating.

6. A method for increasing the image quality of phase-contrast images in an X-ray interferometer that makes use of the Talbot effect and comprises a phase grating and an analysis grating, wherein the method comprises, when the analysis grating is arranged perpendicular with respect to X-ray radiation to be analyzed, inclining the phase grating with respect to the X-ray radiation, the inclination of the phase grating with respect to the X-ray radiation corresponding to a rotation of the phase grating about a grating central axis which runs parallel to grating ribs.

7. A method for producing grating structures inclined on a substrate of a phase grating, corresponding to a rotation of individual grating ribs about their respective longitudinal axis which is arranged parallel to a grating central axis, in which method a phase grating and an analysis grating for an X-ray interferometer are produced starting from the same master mask, wherein the method comprises
using a master mask which has a period of the analysis grating,
creating the analysis grating by direct perpendicular exposure, and
creating the phase gratin& by oblique exposure or oblique arrangement at an angle, by a projection with a grating period.

8. The method of claim 7, wherein the phase and analysis gratings are produced from master masks made by electron beam lithography.

9. A unit, instrument or system selected from an X-ray-based system used in medical engineering, an instrument for non-destructive testing of materials and components, a gantry unit of a computed tomography scanner, an X-ray optical unit of a micro-CT instrument, and an X-ray optical system for medical radiography or angiography, wherein the unit, instrument or system makes use of the Talbot effect and comprises a phase grating and an analysis grating, where, when the analysis grating is arranged to be perpendicular to X-ray radiation to be analyzed, the phase grating is inclined with respect to the X-ray radiation, the inclination of the phase grating with respect to the X-ray radiation corresponding to a rotation of the respective phase grating about a grating central axis which runs parallel to grating ribs.

10. The unit, instrument or system of claim 9, which is an X-ray-based system used in medical engineering.

11. The unit, instrument or system of claim 9, which is an instrument for non-destructive testing of materials and components.

12. The unit, instrument or system of claim 9, which is a gantry unit of a computed tomography scanner.

13. The unit, instrument or system of claim 9, which is an X-ray optical unit of a micro-CT instrument.

14. The unit, instrument or system of claim 9, which is an X-ray optical system for medical radiography or angiography.

* * * * *